United States Patent
Weaver

(10) Patent No.: US 10,517,651 B1
(45) Date of Patent: Dec. 31, 2019

(54) FACET JOINT COMPRESSION SYSTEM FOR SPINAL STABILIZATION

(71) Applicant: Medlastics LLC, Roanoke, VA (US)

(72) Inventor: Edgar N. Weaver, Roanoke, VA (US)

(73) Assignee: MEDLASTICS LLC, Roanoke, VA (US)

( * ) Notice: Subject to any disclaimer, the term of this patent is extended or adjusted under 35 U.S.C. 154(b) by 0 days.

(21) Appl. No.: 16/541,287

(22) Filed: Aug. 15, 2019

Related U.S. Application Data

(60) Provisional application No. 62/758,847, filed on Nov. 12, 2018.

(51) Int. Cl.
| | | |
|---|---|---|
| *A61B 17/70* | (2006.01) | |
| *A61B 90/00* | (2016.01) | |
| *A61F 2/44* | (2006.01) | |

(52) U.S. Cl.
CPC ...... *A61B 17/7064* (2013.01); *A61B 17/7002* (2013.01); *A61B 90/06* (2016.02); *A61B 17/7067* (2013.01); *A61B 2090/061* (2016.02); *A61F 2/4405* (2013.01)

(58) Field of Classification Search
CPC ............ A61B 17/7064; A61B 17/7002; A61B 17/7067; A61B 90/06; A61B 2090/061; A61F 2/4405
USPC ........ 606/246–248, 250, 263–265, 276, 277, 606/284, 301, 305–308, 310, 319, 74, 606/324, 325, 328
See application file for complete search history.

(56) References Cited

U.S. PATENT DOCUMENTS

| | | | | |
|---|---|---|---|---|
| 5,676,703 | A * | 10/1997 | Gelbard | A61B 17/7032 411/383 |
| 6,974,479 | B2 * | 12/2005 | Trieu | A61B 17/70 606/247 |
| 9,393,058 | B2 * | 7/2016 | Aubin | A61B 17/562 |
| 2002/0169451 | A1 * | 11/2002 | Yeh | A61B 17/70 606/276 |
| 2004/0225289 | A1 * | 11/2004 | Biedermann | A61B 17/7035 606/257 |
| 2005/0119748 | A1 * | 6/2005 | Reiley | A61B 17/1671 623/17.11 |
| 2008/0255619 | A1 * | 10/2008 | Schneiderman | A61B 17/7007 606/276 |
| 2009/0318968 | A1 * | 12/2009 | Duggal | A61B 17/7026 606/250 |
| 2010/0274291 | A1 * | 10/2010 | McClellan, III | A61B 17/7004 606/276 |
| 2010/0305616 | A1 * | 12/2010 | Carbone | A61B 17/7044 606/264 |
| 2016/0183986 | A1 * | 6/2016 | Abdou | A61B 17/7064 606/247 |
| 2016/0199113 | A1 * | 7/2016 | Penzimer | A61B 17/0642 606/304 |
| 2018/0008321 | A1 * | 1/2018 | Stern | A61B 17/7002 |

* cited by examiner

*Primary Examiner* — Pedro Philogene
*Assistant Examiner* — David C Comstock
(74) *Attorney, Agent, or Firm* — Peter J. Van Bergen

(57) ABSTRACT

A facet joint compression system includes a rigid post having a longitudinal axis. A rigid arm has a sleeve, a cantilever coupled to the sleeve, and a plate coupled to the cantilever. The sleeve is fitted over the post. A retainer is coupled to the post for applying an axial force to the sleeve wherein the axial force is parallel to the longitudinal axis of the post and is transferred to the plate by the cantilever.

31 Claims, 7 Drawing Sheets

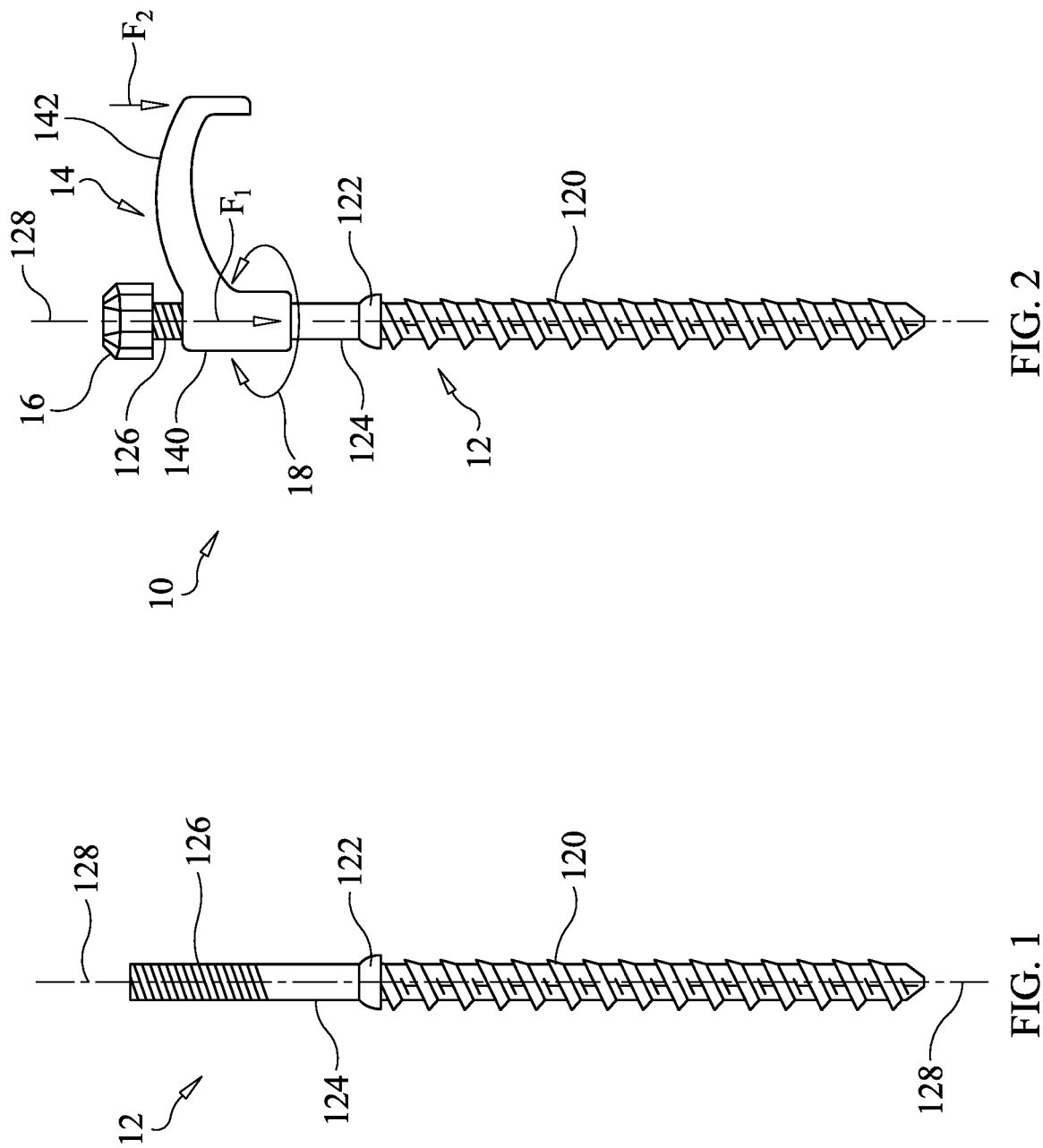

FACET JOINT COMPRESSION SYSTEM FOR SPINAL STABILIZATION

Pursuant to 35 U.S.C. § 119, the benefit of priority from provisional application 62/758,847, with a filing date of Nov. 12, 2018, is claimed for this non-provisional application.

FIELD OF THE INVENTION

The invention relates generally to hardware used in spinal treatment protocols, and more particularly to a facet joint compression system that stabilizes a spine or portion thereof for a variety of spinal treatment procedures.

BACKGROUND OF THE INVENTION

Spinal fusion is a treatment protocol for a variety of spine conditions to include unstable spondylolisthesis, degenerative disc disease, or recurrent disc herniations that lead to a breakdown or deterioration in the integrity of one or more facet joints that connect the vertebrae of the spine. A variety of hardware and techniques can be used to achieve bony spinal fusion depending on the underlying cause. In general a hardware system is used to position and fix the spine in accordance with a treatment plan, and to facilitate the bony fusion process after graft material is placed where appropriate for the ultimate integration of bone masses. Currently, spinal fusion hardware may include a plurality of screws (known as pedicle screws) with each such pedicle screw being anchored in a patient's vertebral pedicle. These pedicle screws serve as anchors and attachment points for rod(s), cable(s), and/or band(s).

The combination of pedicle screws and elements attached thereto stabilizes or fixes a spine's joint(s) as required for the particular treatment protocol. Even the most minor of spinal fusion procedures can require four or more pedicle screws and connecting rods. Unfortunately, each pedicle screw installation, along with conventional rods attached thereto, requires considerable soft tissue dissection/distraction, introduces injury risks, and can cause cracks or breaks in a patient's pedicle that require alterations in a treatment plan and/or consequential spine damage.

SUMMARY OF THE INVENTION

Accordingly, it is an object of the present invention to provide hardware for use in spinal treatments that minimizes the number of pedicle screws and obviates the need for conventional rods.

Another object of the present invention is to provide hardware that is readily adapted for use in a variety of spinal treatment protocols.

Still another object of the present invention to provide hardware that can be used by itself and/or with conventional screw/rod systems for spinal stabilization and/or spinal fusion.

Other objects and advantages of the present invention will become more obvious hereinafter in the specification and drawings.

In accordance with the present invention, a facet joint compression system includes a rigid post having a longitudinal axis. A rigid arm has a sleeve, a cantilever coupled to the sleeve, and a plate coupled to the cantilever. The sleeve is fitted over a portion of the post. A retainer is coupled to the post for applying an axial force to the sleeve wherein the axial force is parallel to the longitudinal axis of the post and is transferred to the plate by the cantilever.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 1 is an isolated side view of a pedicle post in accordance with an embodiment of the present invention;

FIG. 2 is a side view of a pedicle post and compression arm facet joint stabilization system in accordance with an embodiment of the present invention;

DETAILED DESCRIPTION OF THE INVENTION

Figure 3:
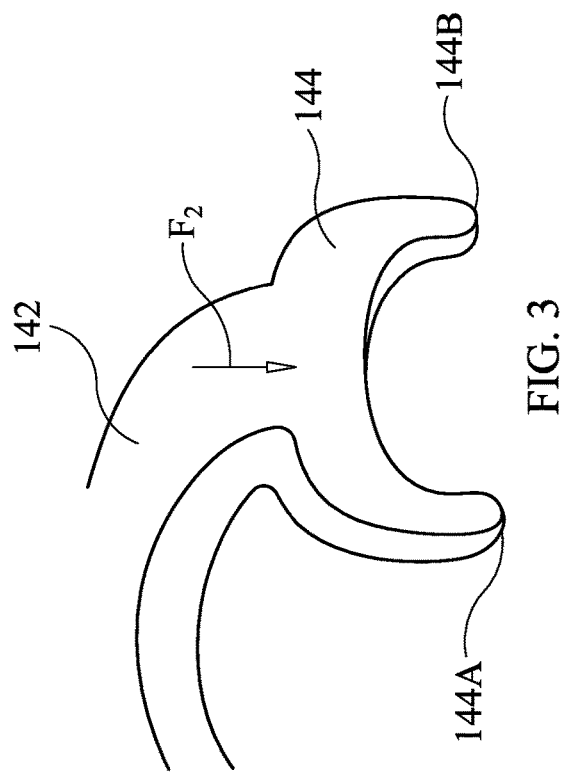
FIG. 3 is a perspective of the outboard end of the compression arm configured with a fixed two-contact-point plate in accordance with an embodiment of the present invention.

Referring now to the drawings, simultaneous reference will be made to FIGS. 1 and 2 where FIG. 2 illustrates a pedicle post and compression arm facet joint stabilization system in accordance with an embodiment of the present invention that is referenced generally by numeral 10. The term "stabilization" as used herein indicates that the present invention can be used as the stabilizing element in spinal fusion treatments employing both hardware and bone graft material. However, the system of the present invention can also be used in stabilizing the spine in applications that increase structural integrity but do not use bony fusion of vertebra using bone graft material as will be explained further below. Such applications preserve some element of motion of the vertebral segments but with reduction of that motion.

In the illustrated embodiment, facet joint stabilization system 10 includes a rigid pedicle post 12 (shown in isolation in FIG. 1), a rigid compression arm 14, and a retainer 16 such as a locking nut (as shown) in threaded engagement with pedicle post 12. It is to be understood that the materials used for facet joint stabilization system 10 can be any acceptable medical-grade material that satisfies the structural and functional requirements of the present invention.

Pedicle post 12 is a rigid element that can be of unibody construction or assembled using multiple parts without departing from the scope of the present invention. Pedicle post 12 includes a screw portion 120, an axial limit stop 122 (e.g., one or more radially-extending protuberances such as the illustrated continuous annular flange, distributed protuberances, etc.), a non-threaded portion 124, and a threaded end 126. Screw portion 120 is the portion of pedicle post 12 that will be screwed into a patient's pedicle (not shown) up to limit stop 122. Pedicle post 12 can be manufactured with a variety of lengths of screw portion 120, thread designs, number of threads, etc., without departing from the scope of the present invention. Axially adjacent to limit stop 122 is non-threaded portion 124 that will facilitate rotation of compression arm 14 about the longitudinal axis 128 of pedicle post 12 during the installation of facet joint stabilization system 10. Threaded end 126 cooperates with retainer/nut 16 such that retainer/nut 16 retains compression arm 14 on pedicle post 12 and provides a desired amount of an axial pressure force to compression arm 14 during installation of facet joint stabilization system 10 as will be explained further below.

Compression arm 14 includes a post-cooperating sleeve 140, a shaped cantilever 142 (e.g., arched in the illustrated embodiment), and a plate 144 for engaging a facet joint complex (not shown) which includes the inferior articular process and facet joint proper. Compression arm 14 can be completely rigid (as shown) or can include a movable spine-engaging end plate as will be explained further below. Sleeve 140 is configured to slide axially over and along threaded end 126 and non-threaded portion 124 of pedicle post 12. During installation, portions 124 and 126 are configured such that sleeve 140 can be rotated about the pedicle post's longitudinal axis 128 as indicated by two-headed arrow 18.

Shaped cantilever 142 is rigid and is rigidly coupled on its inboard end to sleeve 140. For example, cantilever 142 can be integrated with sleeve 140. The outboard end of cantilever 142 is terminated in a spine-engaging end plate 144 that, in use, will ultimately engage a spinal facet joint complex (not shown) as will be explained further below. In the illustrated embodiment, plate 144 is rigid and is rigidly coupled to (e.g., integrated with) the outboard end of cantilever 142. However, plate 144 could also be pivotally coupled to the outboard end of cantilever 142 as will be explained further below. In all embodiments of the present invention, end plate 144 transfers an axial force applied to sleeve 140 along longitudinal axis 128 to a facet joint complex with which plate 144 is engaged. While plate 144 can be disposed at an angle (for fitting purposes) relative to longitudinal axis 128, the transfer of the axial force will occur parallel to longitudinal axis 128 of pedicle post 12 when sleeve 140 is fitted on/over post 12. Adjustments to the direction of the axial force can be made only if the post angle is varied relative to the axis of the pedicle as shown in the FIG. 14 embodiment.

Cantilever 142 is shaped (e.g., arched) to reduce the amount of pedicle post 12 (i.e., the combined axial length of stop 122, non-threaded portion 124, and threaded portion 126) extending out from a patient's pedicle, while also allowing cantilever 142 to go over a degenerative hypertrophic facet joint (not shown). That is, cantilever 142 presents a concave shape when referenced to screw portion 120 or as referenced to a patient's spine when pedicle post 12 is screwed into a spine bone as will be described further below. It is to be understood that compression arm 14 could be manufactured with a variety of arch shapes for its cantilever to accommodate different treatment scenarios without departing from the scope of the present invention.

Plate 144 can be configured in a variety of ways without departing from the scope of the present invention. For example, in the illustrated embodiment, plate 144 is rigidly coupled to the outboard end of cantilever 142 and is defined by two contact teeth or points 144A and 144B as shown in FIG. 3. In use and as will described below, contact teeth or points 144A and 144B will engage the groove found at the junction of a spine facet joint and its adjoining interior articular process.

Figure 4:
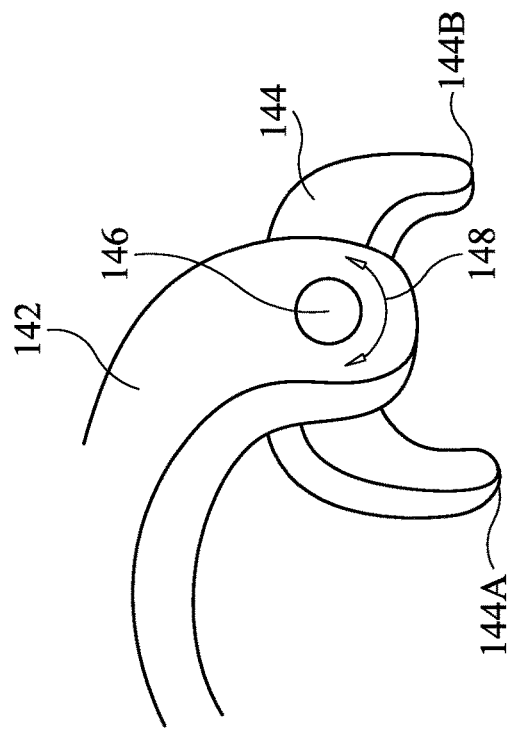
FIG. 4 is a perspective view of the outboard end of the compression arm configured with a pivoting two-contact-point plate in accordance with another embodiment of the present invention.

As mentioned above, plate 144 could also be pivotally coupled to the outboard end of cantilever 142 as illustrated in FIG. 4. More specifically, plate 144 is pivotally coupled to the outboard end of cantilever 142 by means of, for example, a pivot pin 146. In this embodiment, plate 144 can rotate in the plane of the plate as indicated by two-headed arrow 148 to thereby allow plate 144 to adapt to uneven spinal groove surfaces to ensure good contact between teeth/points 144A and 144B and a facet joint complex, while plate 144 remains essentially parallel to longitudinal axis 128 of pedicle post 12. For other treatment applications, it may be necessary for plate 144 to pivot in a different plane or in multiple planes. In such cases, pivot motion of plate 144 could be provided by a ball joint (not shown) to couple plate 144 to cantilever 142. Accordingly, it is to be understood that the type of pivot coupling/motion of plate 144 relative to cantilever 142 is not a limitation of the present invention.

Figure 5:
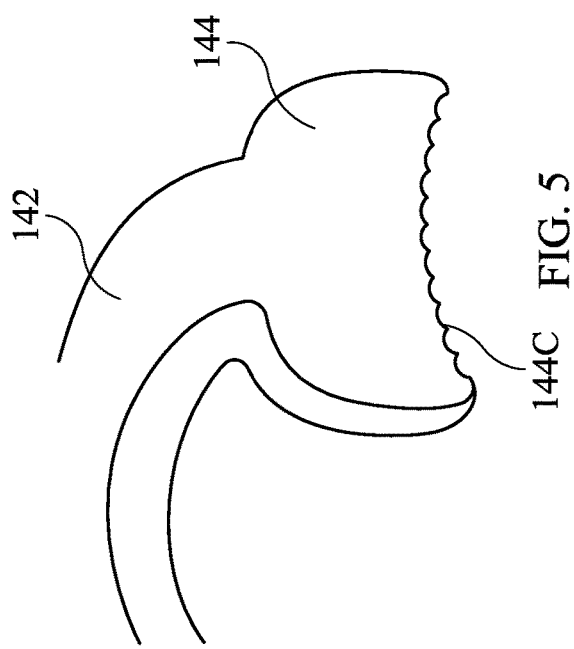
FIG. 5 is a perspective view of the outboard end of the compression arm configured with a fixed serrated-edge plate in accordance with yet another object of the present invention.
Figure 6:
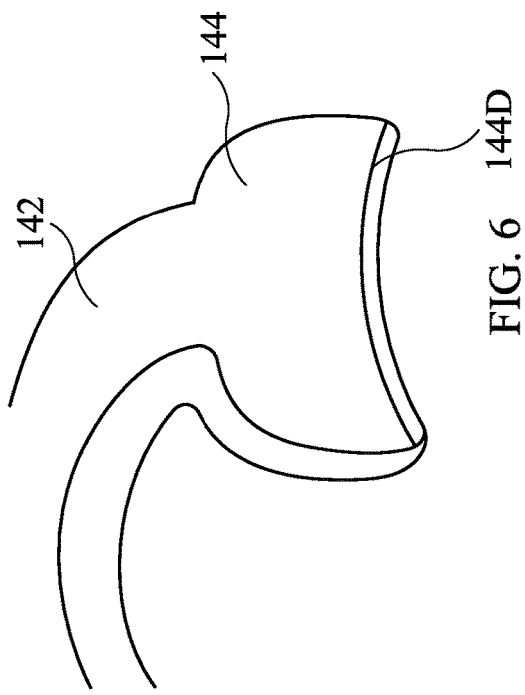
FIG. 6 is a perspective view of the outboard end of the compression arm configured with a fixed conforming-edge plate in accordance with still another embodiment of the present invention.

Plate 144 is not limited to providing only two points of contact with a facet. For example, FIG. 5 illustrates a plate 144 having a serrated edge 144C to define a greater plurality of teeth to increase the number of potential contact points. The serrated-edge plate can be fixedly coupled to the outboard end of cantilever 142 (as shown) or pivotally coupled thereto as shown in FIG. 4 without departing from the scope of the present invention. Another option for plate 144 is illustrated in FIG. 6 where a contact edge 144D of plate 144 is made from a conformable material that assumes the shape of an engaged bone to assure full contact therewith. The conforming-edge plate can be fixedly coupled to the outboard end of cantilever 142 (as shown) or pivotally coupled thereto as shown in FIG. 4 without departing from the scope of the present invention.

In use of facet joint stabilization system 10, pedicle post 12 has its screw portion 120 installed in a pedicle (not shown) up to limit stop 122. Compression arm 14 is slid onto pedicle post 12, and then is moved along post 12 and rotated thereon until plate 144 is resting on a groove medial to a facet joint in accordance with a treatment plan. In general, a properly sized compression arm 14 will ensure that there is a gap between sleeve 140 and axial stop 122 when end plate 144 rests on bone of the facet joint complex. Referring again to FIG. 2, retainer/nut 16 is threaded onto threaded end 126 of pedicle post 12 and torqued down to apply an axial pressure force "$F_1$" to sleeve 140. As this occurs, a compression force "$F_2$" is applied to the facet joint complex through plate 144 and its contact teeth/points 144A and 144B (or any other of the contact points or edges defined by plate 144). The design and construction of stabilization system 10 assures that the resultant compression force $F_2$ is parallel to the applied force $F_1$, while the rigid nature of compression arm 14 assures that the amount of force $F_2$ applied through plate 144 is approximately the same as the amount of force $F_1$ applied to sleeve 140. Since the amount of force applied is readily calibrated to a tightening torque applied to retainer/nut 16, the present invention will allow a surgeon to precisely set a stabilization system for a desired amount of force at a facet joint complex to satisfy treatment requirements and joint complex bone integrity needs. To maintain the requisite application of force after installation, retainer/nut 16 can be lock nut. However, other types of compression force application and/or retention systems could be used without departing from the scope of the present invention.

Figure 7:
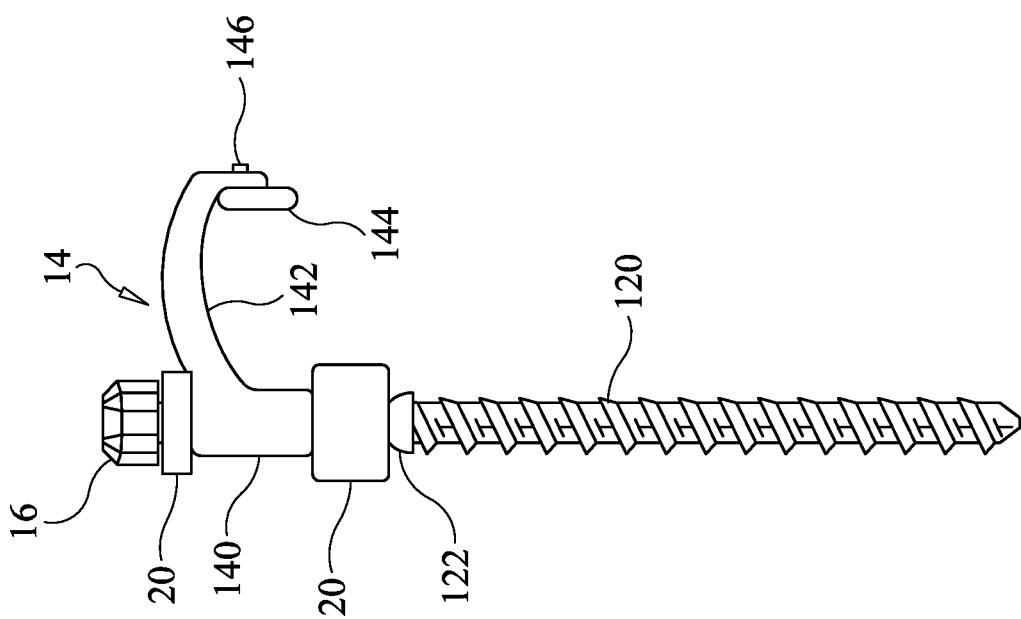
FIG. 7 is a side-view of a pedicle post and compression arm facet joint stabilization system that includes compressible bumpers in accordance with another embodiment of the present invention.

While some treatment procedures require a rigid stabilization with bony fusion using bone graft material, other treatment protocols would desirably prefer that the spinal treatment hardware provided increased stability but with preservation of some degree of facet joint motion. In such treatments, graft material would not be used between some or all of the vertebrae being stabilized. The present invention can provide this capability as illustrated in FIG. 7 where elastic or resilient bumpers 20 can be placed above and/or below sleeve 140 on pedicle post 12 to effectively act as a compression spring. Each resilient bumper 20 could be configured as a washer (e.g., a Belleville washer, a sleeve of elastic material, etc.) that slides onto/over threaded end 126 and/or non-threaded portion 124. The bumper's thickness, material, etc., can be selected to permit a specified amount of elastic axial movement of compression arm 14 as it is retained by retainer/nut 16. Adjustments to the spring force provided by bumper(s) 20 and, therefore, to the compression fixation force being applied to the spine, can also be made by the amount of torque applied to retainer/nut 16 where such torque is readily measurable and calibrated to a desired compression fixation force.

In treatments where there is a transition between bone-fused (instrumented) and unfused (non-instrumented) vertebrae, the present invention equipped with springs (such as bumpers 20) can provide stabilization with increased structural integrity but with preservation of some joint motion. Over one or more segments of such a transition, a patient's spine can be gently transitioned between fused (rigid) and unfused (normal or non-instrumented) spinal regions using one or more facet joint stabilization systems of the present invention equipped with springs.

In a dynamic stabilization treatment scenario in which no vertebrae are fused, an array of facet joint stabilization systems of the present invention could be used with each stabilization system being configurable in terms of its compression tension force to provide each system with a unique amount of fixation thereby achieving the goals of spinal stabilization for structural strength enhancement and yet preserving some element of motion. Spring forces can be established by the one or more bumpers 20 with compression tension (or fixation tension) being adjusted using retainer/nut 16 with measureable torque application. Accordingly, the present invention provides a new treatment paradigm that would provide for fixation tension adjustments over time as a patient's needs change. Such adjustments could be made using very small incisions to provide a surgeon with access to one or more retainer/nut 16 where retainer/nut 16 can be loosened to decrease fixation tension and increase motion, or tightened to increase fixation tension and decrease motion.

Figure 8:
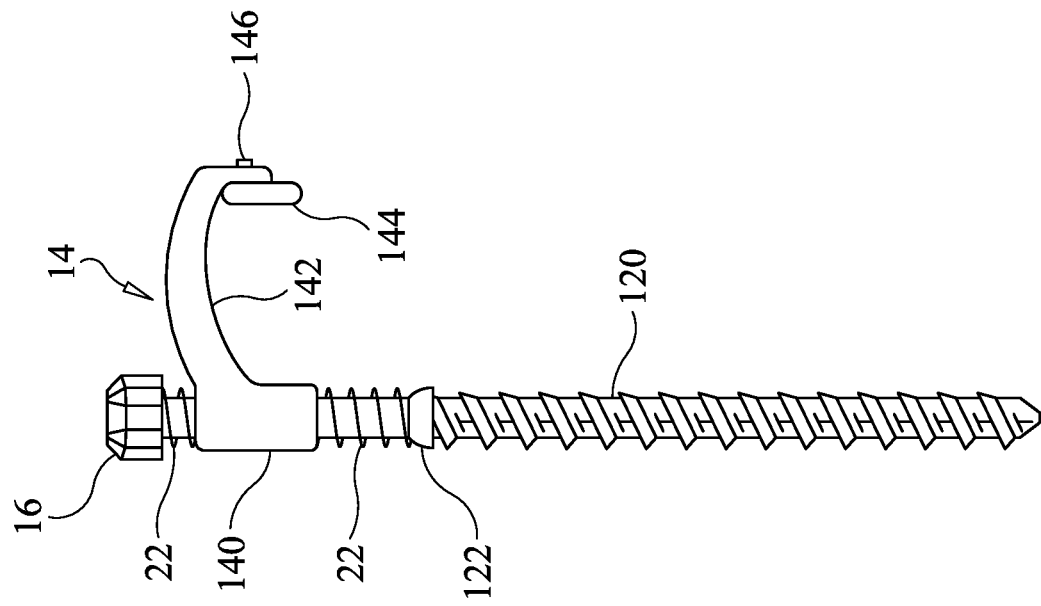
FIG. 8 is a side-view of a pedicle post and compression arm facet joint stabilization system that includes coil springs in accordance with another embodiment of the present invention.
Figure 9:
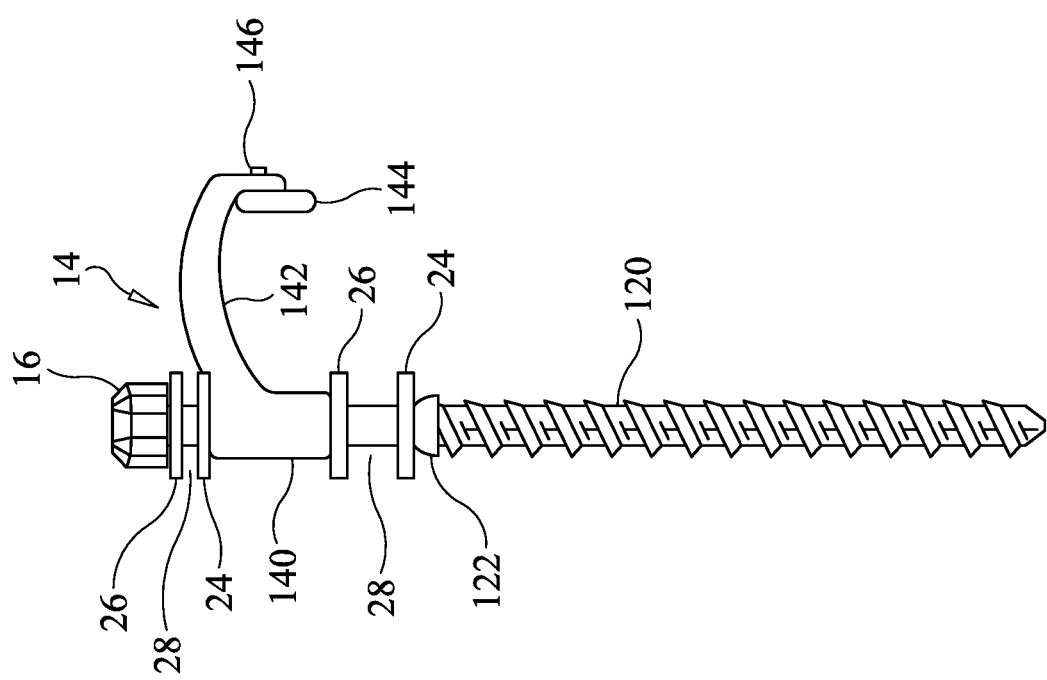
FIG. 9 is a side-view of a pedicle post and compression arm facet joint stabilization system that includes repelling magnets in accordance with another embodiment of the present invention.

The above-described spring forces can be provided by spring elements other than bumpers 20. For example, FIG. 8 illustrates coil springs 22 placed above and/or below sleeve 140 on pedicle post 12. The strength of each coil spring can be tailored to a treatment goal. The retainer/nut 16 can also be used to make adjustments in the spring force as described above. In another embodiment, spring forces are provided by one or more sets of magnets 24/26 placed above and/or below sleeve 140 on pedicle post 12 as shown in FIG. 9. More specifically, magnets 24/26 in each set thereof are positioned on pedicle post 12 to repel one another whereby a gap 28 is defined there between when no compression load is applied to compression arm 14. The strength of the magnets determines the amount of load that must be applied to arm 14 to reduce gap 28. The size of gap 28 can be adjusted through torque adjustment of retainer/nut 16.

Figure 10:
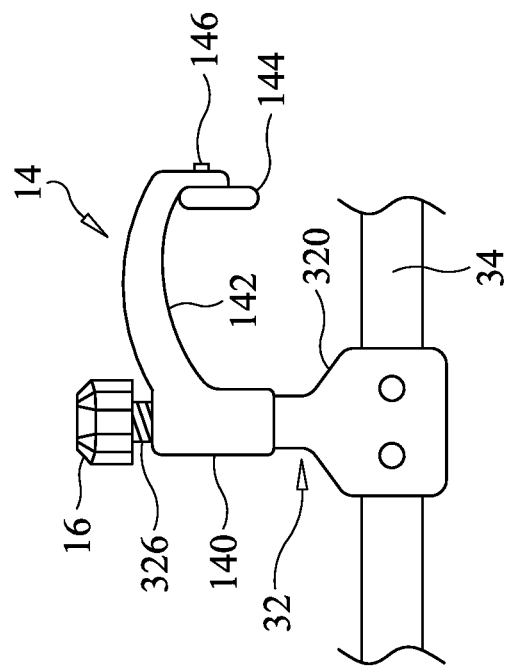
FIG. 10 is a side view of a rod-mounted post and compression arm facet joint stabilization system in accordance with another embodiment of the present invention.

While compression arm 14 has thus far been described for use with a pedicle post 12, the present invention is not so limited. For example and with reference to FIG. 10, compression arm 14 could also be used with a post 32 coupled to a rod 34 of a conventional spinal fusion instrumentation where rod 34 spans between two or more conventional pedicle screws (not shown). More specifically, post 32 has a base 320 configured to be mounted and fixed to rod 34. As in the previously-described embodiment, sleeve 140 of compression arm 14 slides onto post 32 where a threaded end 326 thereof is exposed to provide threaded engagement with retainer/nut 16. Plate 144 can be pivotally coupled (as shown) or fixedly coupled to the outboard end of cantilever 142 as was described previously herein.

Figure 11:
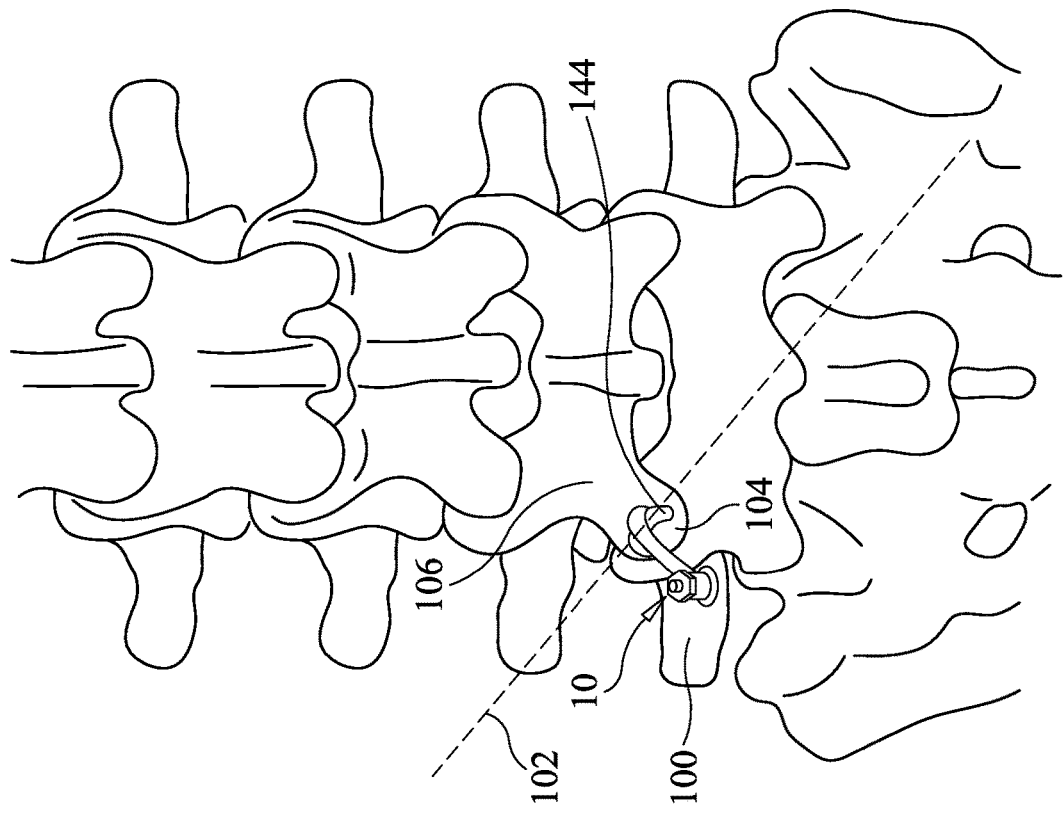
FIG. 11 illustrates a portion of a spine with a single pedicle post and compression arm facet joint stabilization system coupled thereto.
Figure 12:
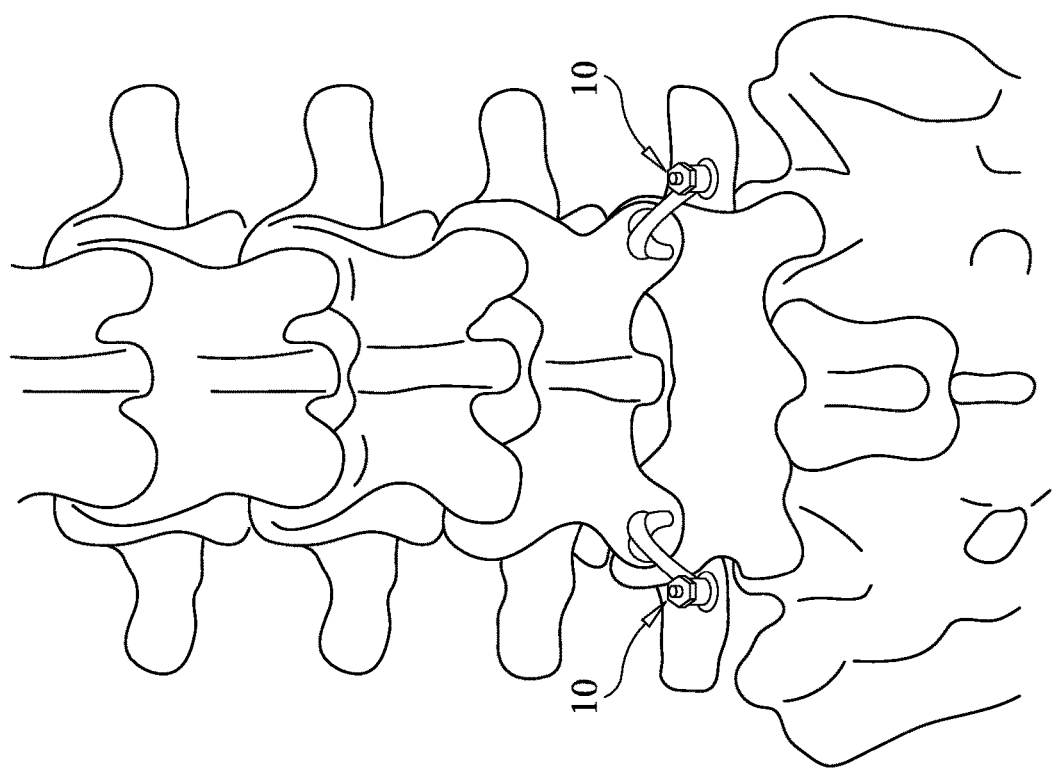
FIG. 12 illustrates a portion of a spine with two pedicle post and compression arm facet joint stabilization systems coupled thereto.
Figure 13:
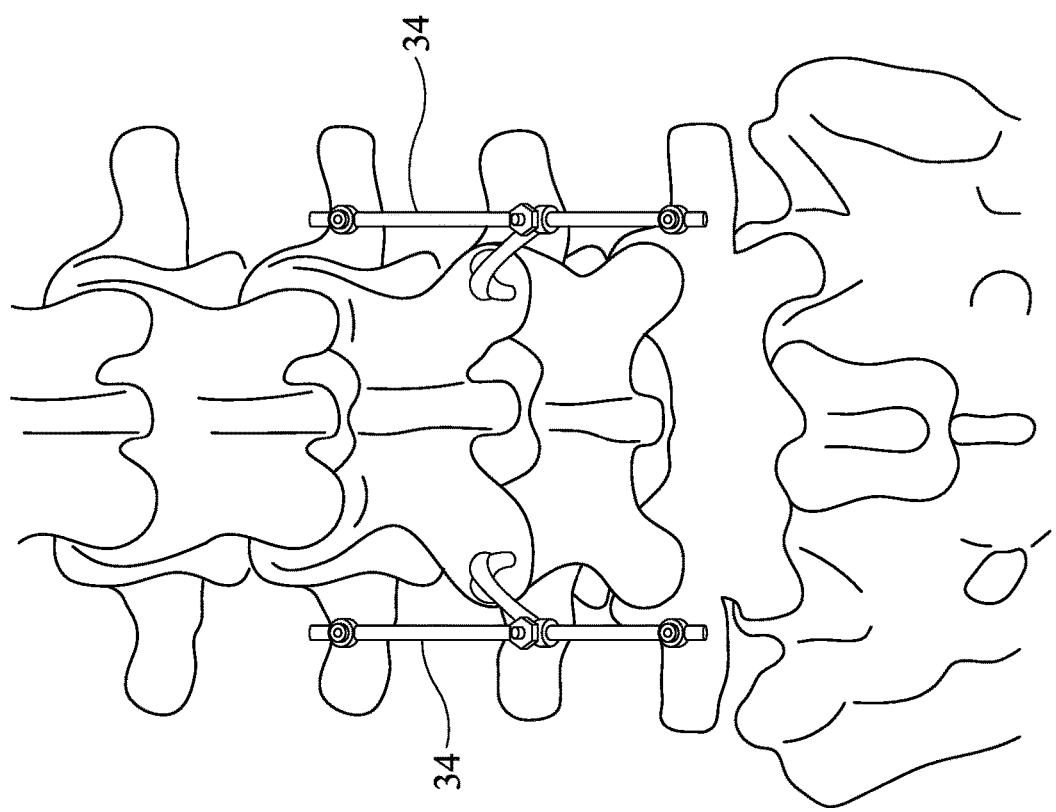
FIG. 13 illustrates a portion of a spine with two rod-mounted post and compression arm facet joint stabilization systems mounted between two traditional pedicle screws.
Figure 14:
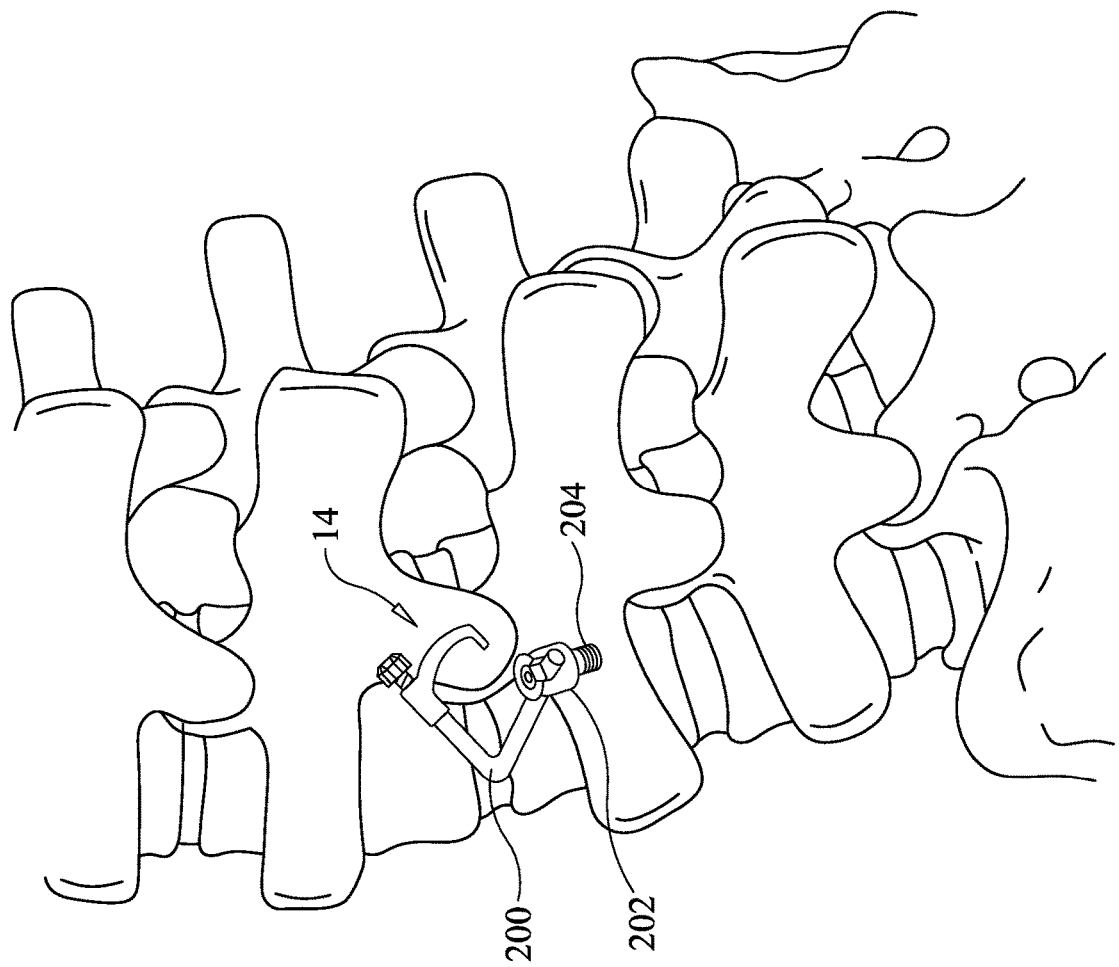
FIG. 14 illustrates a portion of a spine with the present invention's compression arm mounted on a shaped rod coupled to a conventional pedicle screw.

As mentioned above, the present invention can be used in a wide variety of spinal fusion treatments. By way of non-limiting examples, several treatments using hardware in accordance with the present invention are illustrated in FIGS. 11-14. Referring first to FIG. 11, a single facet stabilization system 10 is illustrated with its pedicle post 12 installed in/through the portion of the pedicle 100 that connects the dorsal part of the vertebrae to the anterior part of the vertebrae as would be understood in the art. Plate 144 of compression arm 14 is positioned to engage the groove (occurring along the region illustrated by dashed line 102) that is along the junction of the inferior articular process 104 and the facet proper 106. FIG. 12 illustrates the use of bilateral facet joint stabilization compression using two of systems 10 installed on opposing sides of a spine. FIG. 13 illustrates the use of two rod-mounted facet joint stabilization systems cooperating with conventional rods 34 as described above and shown in FIG. 10. Finally, FIG. 14 illustrates the use of compression arm 14 mounted on the post attached to a shaped rod 200 that is integral with a polyaxial head 202 of a conventional pedicle screw 204.

The advantages of the present invention are numerous. This facet joint stabilization system reduces the number of pedicle screw couplings to a patient's spine thereby reducing soft tissue dissection/distraction, reducing the risk of spinal cracks/breaks, and reducing the amount of hardware that must be left in a patient. Furthermore, the absence of rod application also reduces soft tissue dissection/distraction and simplifies stabilization for mini-invasive application. In addition, the shape (e.g., arch) of the system's compression arm and its end plate provide for the efficient and predictable transference of axial forces applied at the pedicle post to the end plate engaging a facet joint complex. Still further, the present invention can be adapted for use in a variety of treatment protocols to include treatments requiring bone fusion, treatments requiring both bone fusion and transition to unfused vertebrae, and total non-fusion-based treatments requiring spinal stabilization with increased structural integrity but with some degree of motion preservation. The compression arm of the present invention could also be mounted on a post coupled to conventional spinal fusion hardware to provide additional points of stabilization without the need for corresponding pedicle screw installations.

Figure 15:
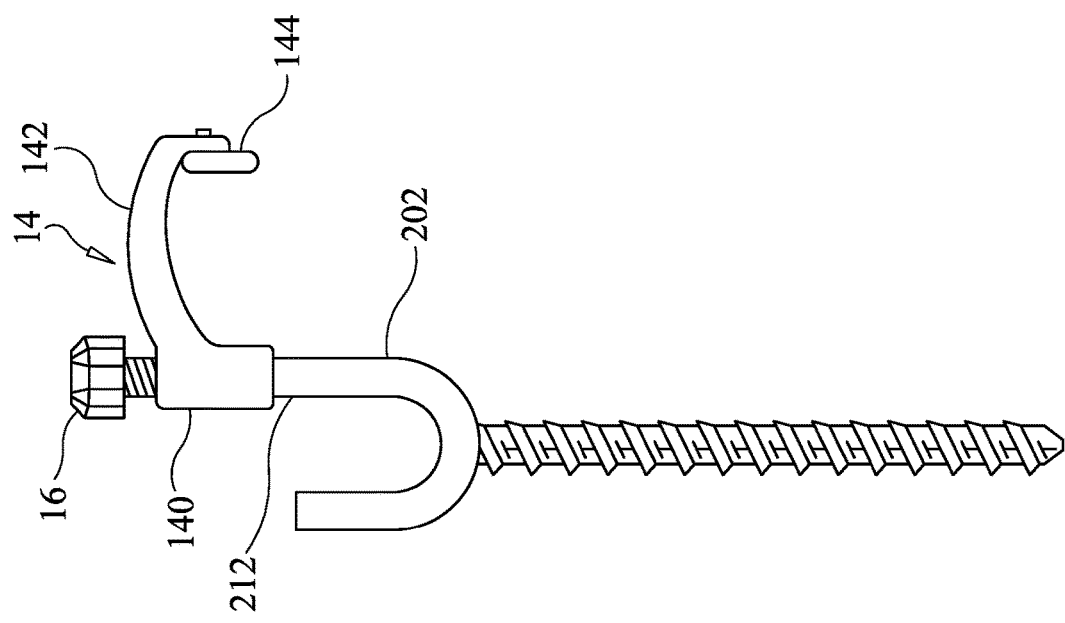
FIG. 15 illustrates a modified polyaxial head of a pedicle screw that includes a post for cooperation with the compression arm in accordance with another embodiment of the present invention.

Although the invention has been described relative to specific embodiments thereof, there are numerous other variations and modifications that will be readily apparent to those skilled in the art in light of the above teachings. For example and with reference to FIG. 15, another embodiment of the present invention is illustrated where a polyaxial head 202 is modified to include an integrated post 212 to support the above-described compression arm 14 and retainer/nut 16. In still other embodiments where a non-threaded portion of the pedicle post was provided, a plurality of indexing regions could be defined for cooperation on the inside of the compression arm's sleeve. In this type of embodiment, the compression arm would be prevented from rotation about the post once the indexing regions engaged one another. It is therefore to be understood that, within the scope of the appended claims, the invention may be practiced other than as specifically described.

What is claimed as new and desired to be secured by Letters Patent of the United States is:

1. A facet joint compression system, comprising:
    a rigid post having a longitudinal axis, said post having an axial end adapted to be installed in a patient's spine;
    a rigid arm having a sleeve, a cantilever coupled to said sleeve, and a plate coupled to said cantilever and adapted to rest on a portion of the patient's spine when said post is installed therein, said sleeve being fitted over a portion of said post; and
    a retainer coupled to said post for applying an axial force to said sleeve wherein the axial force is parallel to said longitudinal axis of said post, is directed towards said axial end of said post, and is transferred to said plate by said cantilever wherein said plate is adapted to apply a compressive force to the portion of the patient's spine.

2. A facet joint compression system as in claim 1, wherein said post includes a screw portion adapted to be screwed into a patient's spine and wherein said sleeve resides on said post adjacent to said screw portion.

3. A facet joint compression system as in claim 1, further comprising at least one radially-extending protuberance coupled to said post.

4. A facet joint compression system as in claim 3, further comprising at least one spring disposed between said retainer and said at least one radially-extending protuberance.

5. A facet joint compression system as in claim 4, wherein said spring is selected from the group consisting of elastic washers, coil springs, and repelling magnets.

6. A facet joint compression system as in claim 1, wherein said post and said retainer are in threaded engagement.

7. A facet joint compression system as in claim 1, wherein said plate has an outboard edge adapted to engage spinal bone when the axial force is applied to said sleeve.

8. A facet joint compression system as in claim 7, wherein said outboard edge includes a plurality of teeth.

9. A facet joint compression system as in claim 7, wherein said outboard edge comprises a conformable material.

10. A facet joint compression system as in claim 1, wherein said plate is pivotally coupled to said cantilever.

11. A facet joint compression system as in claim 1, wherein said cantilever is arched between said sleeve and said plate.

12. A facet joint compression system as in claim 1, wherein said sleeve is sized for rotation on said post and about said longitudinal axis thereof.

13. A facet joint compression system, comprising:
    a rigid post having a longitudinal axis, said post having a first axial end and a second axial end, said second axial end adapted to be installed in a patient's spine;
    at least one radially-extending protuberance coupled to said post between said first axial end and said second axial end;
    a rigid arm having a sleeve, an arched cantilever coupled on one end thereof to said sleeve, and a plate coupled to another end of said arched cantilever and adapted to rest on a portion of the patient's spine when said post is installed therein, said sleeve being fitted over said first axial end of said post, wherein said plate is approximately parallel to said longitudinal axis of said post when said sleeve is fitted over said post; and
    a retainer coupled to said post for applying an axial force to said sleeve wherein the axial force is parallel to said longitudinal axis of said post, is directed towards said second axial end of said post, and is transferred to said plate by said arched cantilever wherein said plate is adapted to apply a compressive force to the portion of the patient's spine.

14. A facet joint compression system as in claim 13, wherein said post includes a screw portion extending from said at least one radially-extending protuberance to said second axial end of said post, said screw portion adapted to be screwed into a patient's spine.

15. A facet joint compression system as in claim 13, further comprising at least one spring disposed between said retainer and said at least one radially-extending protuberance.

16. A facet joint compression system as in claim 15, wherein said spring is selected from the group consisting of elastic washers, coil springs, and repelling magnets.

17. A facet joint compression system as in claim 13, wherein said post and said retainer are in threaded engagement.

18. A facet joint compression system as in claim 13, wherein said plate has an outboard edge adapted to engage spinal bone when the axial force is applied to said sleeve.

19. A facet joint compression system as in claim 18, wherein said outboard edge includes a plurality of teeth.

20. A facet joint compression system as in claim 18, wherein said outboard edge comprises a conformable material.

21. A facet joint compression system as in claim 13, wherein said plate is pivotally coupled to said arched cantilever.

22. A facet joint compression system as in claim 13, wherein said sleeve is sized for rotation on said post and about said longitudinal axis thereof.

23. A facet joint compression system, comprising:
- a rigid post having a longitudinal axis, said post having a first axial end, a second axial end, and an annular flange between said first axial end and said second axial end, said second axial end adapted to be installed in a patient's spine;
- a rigid arm having a sleeve, an arched cantilever coupled on one end thereof to said sleeve, and a plate coupled to another end of said arched cantilever and adapted to rest on a portion of the patient's spine when said post is installed therein, said sleeve being fitted over said first axial end of said post, wherein said plate is parallel to said longitudinal axis of said post when said sleeve is fitted over said post; and
- a retainer threaded onto said post for applying an axial force to said sleeve wherein the axial force is parallel to said longitudinal axis of said post, is directed towards said second axial end of said post, and is transferred to said plate by said arched cantilever wherein said plate is adapted to apply a compressive force to the portion of the patient's spine.

24. A facet joint compression system as in claim 23, wherein said post includes a screw portion extending from said annular flange to said second axial end of said post, said screw portion adapted to be screwed into a patient's spine.

25. A facet joint compression system as in claim 23, further comprising at least one spring disposed between said retainer and said annular flange.

26. A facet joint compression system as in claim 25, wherein said spring is selected from the group consisting of elastic washers, coil springs, and repelling magnets.

27. A facet joint compression system as in claim 23, wherein said plate has an outboard edge adapted to engage spinal bone when the axial force is applied to said sleeve.

28. A facet joint compression system as in claim 27, wherein said outboard edge includes a plurality of teeth.

29. A facet joint compression system as in claim 27, wherein said outboard edge comprises a conformable material.

30. A facet joint compression system as in claim 23, wherein said plate is pivotally coupled to said arched cantilever.

31. A facet joint compression system as in claim 23, wherein said sleeve is sized for rotation on said post and about said longitudinal axis thereof.

* * * * *